US012599654B2

(12) United States Patent
Kong et al.

(10) Patent No.: US 12,599,654 B2
(45) Date of Patent: Apr. 14, 2026

(54) IMMUNOGENIC PEPTIDE FRAGMENTS OF METALLOPROTEASE ADAMTS-7 AND USES THEREOF IN ANTI-ATHEROSCLEROSIS AND RELATED DISEASES

(71) Applicant: BEIJING KIMWAY BIOTECH CO. LTD, Beijing (CN)

(72) Inventors: Wei Kong, Beijing (CN); Yi Fu, Beijing (CN); Jingang Zheng, Beijing (CN); Zihan Ma, Beijing (CN); Yuhua Liao, Beijing (CN); Xiao Chen, Beijing (CN); Chenfeng Mao, Beijing (CN)

(73) Assignee: BEIJING KIMWAY BIOTECH CO. LTD, Beijing (CN)

( * ) Notice: Subject to any disclaimer, the term of this patent is extended or adjusted under 35 U.S.C. 154(b) by 1062 days.

(21) Appl. No.: 17/642,837

(22) PCT Filed: Aug. 20, 2020

(86) PCT No.: PCT/CN2020/110233
§ 371 (c)(1),
(2) Date: Mar. 14, 2022

(87) PCT Pub. No.: WO2021/057346
PCT Pub. Date: Apr. 1, 2021

(65) Prior Publication Data
US 2022/0370578 A1 Nov. 24, 2022

(30) Foreign Application Priority Data
Sep. 25, 2019 (CN) .......................... 201910914243.9

(51) Int. Cl.
| | |
|---|---|
| C07K 7/06 | (2006.01) |
| A61K 39/00 | (2006.01) |
| A61P 9/10 | (2006.01) |
| C07K 17/02 | (2006.01) |
| C07K 14/81 | (2006.01) |
| C12N 9/64 | (2006.01) |

(52) U.S. Cl.
CPC ........ *A61K 39/001158* (2018.08); *A61P 9/10* (2018.01); *C07K 7/06* (2013.01); *C07K 17/02* (2013.01); *A61K 2039/6037* (2013.01); *A61K*

*2039/6075* (2013.01); *A61K 2039/6081* (2013.01); *C07K 14/8146* (2013.01); *C12N 9/6489* (2013.01); *C12Y 304/24* (2013.01)

(58) Field of Classification Search
CPC .................. C07K 14/8146; C07K 7/06; A61K 39/001158; C12Y 304/24
See application file for complete search history.

(56) References Cited

PUBLICATIONS

Record for GenBank Accession No. VFV25269.1, dated Mar. 25, 2019, no author indicated, 1 page as printed; available at www.ncbi.nlm.gov/protein/VFV25269.*
First Office Action issued in corresponding Chinese Application No. 201910914243.9; mailed Jun. 10, 2021; 9 pgs.
International Search Report issued in corresponding International Application No. PCT/CN2020/110233; mailed Nov. 25, 2020; 12 pgs.

* cited by examiner

Primary Examiner — Zachary C Howard
(74) Attorney, Agent, or Firm — HAUPTMAN HAM, LLP

(57) ABSTRACT

Immunogenic peptide fragments of metalloprotease ADAMTS-7 including a first short peptide, which is any one of the followings: a short peptide having the amino acid sequence shown in SEQ ID NO: 1 in the sequence listing; a short peptide having the amino acid sequence shown in SEQ ID NO: 2 in the sequence listing; a short peptide having the amino acid sequence shown in SEQ ID NO: 3 in the sequence listing; a short peptide having the amino acid sequence shown in SEQ ID NO: 4 in the sequence listing. The description includes uses of conjugates containing the above short peptides and vaccines containing the conjugates. The vaccines containing the short peptides can remarkably inhibit the intimal neogenesis in the vascular restenosis mouse models and the occurrence of atherosclerosis in high-fat-fed mice, and can be used for the prevention or treatment of atherosclerosis and/or vascular restenosis.

3 Claims, 4 Drawing Sheets
Specification includes a Sequence Listing.

FIG. 3A Subcutaneous injection Injury operation Sampling

Titer detection

FIG. 3 C   KLH   DP-9   CD-9   FIG. 3D

Subcutaneous injection

High-fat diet 0W 2W 3W 4W 9W 12W 13W 15W 18W

Titer detection

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence -continued

```
<220> FEATURE:
<223> OTHER INFORMATION: Synthesized

<400> SEQUENCE: 1

Asp Cys Glu Pro Val Gly Lys Arg Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Cys Leu Asp Asp Pro Pro Ala Lys Asp
1               5

<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Cys Asn Met Lys Gly Asp Ala His Pro
1               5

<210> SEQ ID NO 4
<211> LENGTH: 8
<212> TYPE: PRT
<213> ORGANISM: Artificial Sequence
<220> FEATURE:
<223> OTHER INFORMATION: Synthesized

<400> SEQUENCE: 4

Cys Ser Ser Gly Arg Asp Glu Asp
1               5
```

IMMUNOGENIC PEPTIDE FRAGMENTS OF METALLOPROTEASE ADAMTS-7 AND USES THEREOF IN ANTI-ATHEROSCLEROSIS AND RELATED DISEASES

RELATED APPLICATIONS

The present application is a U.S. National Phase of International Application Number PCT/CN2020/110233 filed Aug. 20, 2020 and claims priority to Chinese Application Number 201910914243.9 filed Sep. 25, 2019.

INCORPORATION BY REFERENCE

The sequence listing provided in the file entitled SQL_Eng_Mod.txt, which is an ASCII text file that was created on Feb. 28, 2022, and which comprises 1,011 bytes, is hereby incorporated by reference in its entirety.

TECHNICAL FIELD

The present invention relates to the fields of biotechnology and medicine, in particular to immunogenic peptide fragments of metalloprotease ADAMTS-7 and uses thereof in anti-atherosclerosis and related diseases.

BACKGROUND OF THE INVENTION

Coronary heart disease is known as "the number one killer of human beings" because of its high morbidity and high mortality, which seriously endangers human health. The main cause of coronary heart disease is atherosclerosis of coronary artery, and its pathological process is due to the abnormal accumulation of lipids in the vascular wall, which leads to the injury of endothelial cells of the vascular wall, proliferation and migration of vascular smooth muscle cells, infiltration of inflammatory cells and so on, and then the formation of plaque protruding into the lumen, which leads to lumen stenosis and insufficient blood supply.

The treatment of coronary heart disease currently focus on the following three strategies: (1) drug therapy; the purpose is to relieve symptoms, reduce the onset of angina pectoris and myocardial infarction, delay the development of coronary atherosclerotic lesions and reduce death from coronary heart disease; lipid-lowering drugs such as statins reduce cardiovascular events by 25% but also increase the risk of new-onset diabetes; the emergence of Ezetimibe or PCSK9 mAb has brought new hope, but they still focus on the strategy of lipid-lowering interventions; however, in terms of the current medical level, there is no drug can cure coronary heart disease, and the treatment of coronary heart disease in fact mainly aims to control the disease state of coronary heart disease, to avoid the deterioration of the disease to cause complications; (2) percutaneous coronary intervention (PCI); in percutaneous transluminal coronary angioplasty (PTCA), a specially designed balloon catheter is delivered through a peripheral artery (femoral or radial artery) to the stenosis site of the coronary artery and then the balloon is inflated to dilate the narrowed lumen and improve blood flow, and a stent is placed in the dilated stenosis site to prevent restenosis; however, there are still risks of stent failure, including stent thrombosis (ST) and in-stent restenosis (ISR); stent thrombosis is a serious clinical complication, and can even lead to elevation myocardial infarction in the thrombus formation segment, with a mortality rate as high as 20%-40%; the occurrence of in-stent restenosis has a great impact on the long-term prognosis after PCI; under the normal endothelial cell barrier, the arterial wall can avoid lipid deposition; however, drug-eluting stents can cause structural and functional impairment of endothelial cells, resulting in delayed endothelial healing and a tendency to form new atherosclerosis. In addition, arterial bypass grafting and minimally invasive techniques in surgical retreatment are not suitable for the treatment of most vascular restenosis due to the difficulty of operation and serious injury. Therefore, new methods are urgently needed to prevent restenosis and thrombosis after dilation.

Because stent and bypass surgery did not make clinicians and patients completely satisfied with the effect, medical scientists from around the world began to study causes of coronary heart disease and vascular stenosis. In recent years, there has been great interest in the development of a vaccine against atherosclerosis. In 1983, Dr. Horváth István from Hungary first discovered the existence of cholesterol antibodies in normal human body, and developed a cholesterol antigen vaccine. In 2002, it was approved by the Hungarian National Medical Administration and entered into human clinical trials. Nearly a decade to date, more than 40,000 patients have received treatment, and remarkable results have been achieved, making mankind stride an important step in the field of cardiovascular disease. Following Dr. Horváth István's development of a cholesterol immunization vaccine in 1983, scientists at Karolinska Institute in Sweden have developed a cholesterol vaccine, which can prevent cholesterol from harming arteries and reduce the incidence of heart disease by two-thirds. In addition, monoclonal antibodies or short peptide vaccines targeting the pathogenic LDL apolipoprotein ApoB100 and the LDLR-degrading enzyme PCSK9 have been developed one after another, and preliminary animal model experiments and preclinical validation are underway. The most likely to be approved for human treatment in the near future is the monoclonal antibody (REGN727) against the proprotein convertase subtilisin/kexin type 9 (PCSK9), and the results of phase I clinical trials showed that low-dose REGN727 can reduce the LDL level of subjects by more than 30%. For patients who cannot tolerate statin therapy, REGN727 has broad clinical application prospects. In addition, short peptide vaccines designed to act on apolipoprotein ApoB100 have shown a certain anti-atherosclerosis effect in experimental animals. These progresses all suggest that the development and design of short peptide vaccines against specific targets and the corresponding monoclonal antibodies produced have potential significance for the prevention and treatment of diseases.

ADAMTS-7 (a disintegrin-like and metalloprotease-7, a disintegrin-like and metalloprotease-7 with thrombospondin type I motif) is a novel metalloprotease cloned in 2004 and belongs to the $Zn^{2+}$-dependent metalloprotease family. The human a disintegrin-like and metalloprotease (ADAMTS) family containing thrombospondin (TSP) type I motif is composed of 19 secreted multi-domain zinc-finger metalloproteases, which can degrade extracellular matrix components (ECM), including procollagen, proteoglycans, and cartilage oligomeric matrix protein (COMP). ADAMTS proteases play an important role in the turnover of extracellular matrix components in various tissues, and the abnormal expression of these enzymes is usually closely related to inflammatory pathological processes, such as tumors and rheumatoid arthritis. Using small interfering RNA silencing, adenovirus overexpression of ADAMTS-7 and construction of ADAMTS-7 gene knockout animal models, it was found that metalloprotease ADAMTS-7 promotes vascular smooth muscle cell migration and neointima formation after vascular injury by degrading cartilage oligomeric matrix protein (COMP) (Wang, L. et al. Adamts-7 mediates vascular smooth muscle cell migration and neointima formation in balloon-injured rat arteries. Circ Res. 2009; 104:688-698), and ADAMTS-7 was also found to inhibit endothelial repair via TSP-1,25 thus promoting neointima formation from a dual mechanism (Kessler T, Zhang L. et al. Adamts-7 inhibits re-endothelialization of injured arteries and promotes vascular remodeling through cleavage of thrombospondin-1. Circulation. 2015; 131:1191-1201).

Currently, there is no report of an effective short peptide vaccine related to ADAMTS-7.

SUMMARY OF THE INVENTION

The technical problem to be solved by the present invention is how to obtain the immunogenic peptide fragment of metalloprotease ADAMTS-7 to prevent or treat atherosclerosis and/or vascular restenosis.

In order to solve the above-mentioned technical problem, the present invention first provides a short peptide, and the short peptide is any one of the following A1) to A4):

A1) a short peptide having the amino acid sequence shown in SEQ ID NO: 1 in the sequence listing;

A2) a short peptide having the amino acid sequence shown in SEQ ID NO: 2 in the sequence listing;

A3) a short peptide having the amino acid sequence shown in SEQ ID NO: 3 in the sequence listing;

A4) a short peptide having the amino acid sequence shown in SEQ ID NO: 4 in the sequence listing.

Specifically, the short peptide is the following A1) or A2):

A1) a short peptide having the amino acid sequence shown in SEQ ID NO: 1 in the sequence listing;

A2) a short peptide having the amino acid sequence shown in SEQ ID NO: 2 in the sequence listing.

More specifically, the short peptide is the short peptide having the amino acid sequence shown in SEQ ID NO: 1 in the sequence listing.

Use of the above-mentioned short peptide also falls within the protection scope of the present invention.

Use of the above-mentioned short peptide of the present invention includes any one of the following B1) to B4):

B1) in the preparation of products for preventing or treating atherosclerosis;

B2) in the preparation of products for preventing or treating vascular restenosis;

B3) in the preparation of products for reducing the neointima area of damaged arteries;

B4) in the preparation of products for reducing the ratio of intima area to media area in damaged arteries.

In the above use, the product can be a drug, a reagent or a vaccine, etc.

The present invention further provides a conjugate of the above short peptide, the conjugate is a complete antigen obtained by coupling the above short peptide and a carrier protein.

In the above conjugate, the carrier protein can be keyhole limpet hemocyanin, recombinant Qβ phage particle protein, recombinant bovine papilloma virus protein, recombinant hepatitis B virus protein or tetanus toxoid.

In the above conjugate, the coupling agent used in the coupling is a heterobifunctional cross-linking agent; specifically, the heterobifunctional cross-linking agent can be SMCC, Sulfo-SMCC or LC-SMCC.

Use of the above-mentioned conjugate is also within the protection scope of the present invention.

Use of the above-mentioned conjugate of the present invention includes any one of the following B1) to B4):

B1) in the preparation of products for preventing or treating atherosclerosis;

B2) in the preparation of products for preventing or treating vascular restenosis;

B3) in the preparation of products for reducing the neointima area of damaged arteries;

B4) in the preparation of products for reducing the ratio of intima area to media area in damaged arteries.

In the above use, the product can be a drug, a reagent or a vaccine, etc.

The present invention further provides a vaccine for preventing or treating atherosclerosis and/or preventing or treating vascular restenosis and/or reducing the neointima area of damaged arteries and/or reducing the ratio of neointima area to neomedia area of damaged arteries.

The above-mentioned vaccine contains the conjugate obtained by coupling the short peptide in any one of the following A1) to A4) with a carrier protein:

A1) a short peptide having the amino acid sequence shown in SEQ ID NO: 1 in the sequence listing;

A2) a short peptide having the amino acid sequence shown in SEQ ID NO: 2 in the sequence listing;

A3) a short peptide having the amino acid sequence shown in SEQ ID NO: 3 in the sequence listing;

A4) a short peptide having the amino acid sequence shown in SEQ ID NO: 4 in the sequence listing.

In the above vaccine, the carrier protein can be keyhole limpet hemocyanin (KLH), recombinant Qβ phage particle protein, recombinant bovine papilloma virus protein, recombinant hepatitis B virus protein or tetanus toxoid.

In the above vaccine, an immune adjuvant is also contained.

In the above vaccine, the immune adjuvant can be, but not limited to, aluminum hydroxide adjuvant, alum adjuvant or Freund's adjuvant.

Use of the above vaccine in the preparation of products for preventing or treating atherosclerosis and/or preventing or treating vascular restenosis and/or reducing the neointima area of damaged arteries and/or reducing the ratio of neointima area to neomedia area of damaged arteries is also within the protection scope of the present invention.

In the above use, the product can be a drug or a reagent.

The present invention further provides a method for preventing or treating atherosclerosis and/or preventing or treating vascular restenosis and/or reducing the neointima area of damaged arteries and/or reducing the ratio of intima area to media area of damaged arteries.

The method for preventing or treating atherosclerosis and/or preventing or treating vascular restenosis and/or reducing the neointima area of damaged arteries and/or reducing the ratio of intima area to media area of damaged arteries of the present invention comprises the step of administering the above conjugate or the above vaccine to an animal to prevent or treat atherosclerosis and/or prevent or treat vascular restenosis and/or reduce the neointima area of damaged arteries and/or reduce the ratio of intima area to media area of damaged arteries.

The above-mentioned short peptide of the present invention comprises a first linking site, and can at least bind to a second linking site of the carrier protein through at least one covalent bond. Recombinant Qβ phage particle protein, recombinant bovine papilloma virus protein, recombinant hepatitis B virus protein, keyhole limpet hemocyanin and tetanus toxoid are used as carrier proteins and these carrier proteins have at least one second linking site. Preferably, the second linking site comprises an amino group, a carboxyl group, and a sulfhydryl group, and is specifically selected from lysine residues, arginine residues, glutamic acid residues, aspartic acid residues and cysteine residues. The ADAMTS-7 short peptide was conjugated to the above carrier protein using a heterobifunctional cross-linking agent to form an ordered and repeat short peptide-carrier vaccine. The short peptide is repeated and displayed at a certain density on the carrier or surface to form a highly antigenic array display, which is conducive to the generation of highly efficient and specific anti-human and mouse ADAMTS-7 immunogenic peptide antibodies, which can effectively block the hydrolase function of ADAMTS-7 and significantly inhibit the intimal neogenesis in vascular restenosis mouse models and the occurrence of atherosclerosis in high-fat-fed mice.

DESCRIPTION OF THE DRAWINGS

In FIGS. 3A-3G, panel 3A is a schematic diagram of ADAMTS-7 vaccine vaccination time points, titer detection time points and guide wire injury operation time point; panel 3B shows the titer detection results of ADAMTS-7 vaccines; panel 3C shows the HE staining results; panel 3D shows the neointima areas of guide wire injury model mice; panel 3E shows the ratios of neointima area to media area of guide wire injury model mice; panel 3F shows the perimeters of the outer elastic plates (i.e., outer perimeters) of guide wire injury model mice; panel 3G shows the media areas of guide wire injury model mice.

DETAILED DESCRIPTION OF THE INVENTION

The present invention is further described in detail hereinafter with reference to specific embodiments, and the given examples are only used to illustrate the present invention, and are not intended to limit the scope of the present invention.

The experimental methods in the following examples are all conventional methods unless otherwise specified.

All the materials and reagents used in the following examples are commercially available unless otherwise specified.

Example 1. Preparation of ADAMTS-7 Vaccines and Titer Detection

1. Screening of Immunogenic Peptide Fragments of Metalloprotease ADAMTS-7

Figures 1A, 1B, 1C:
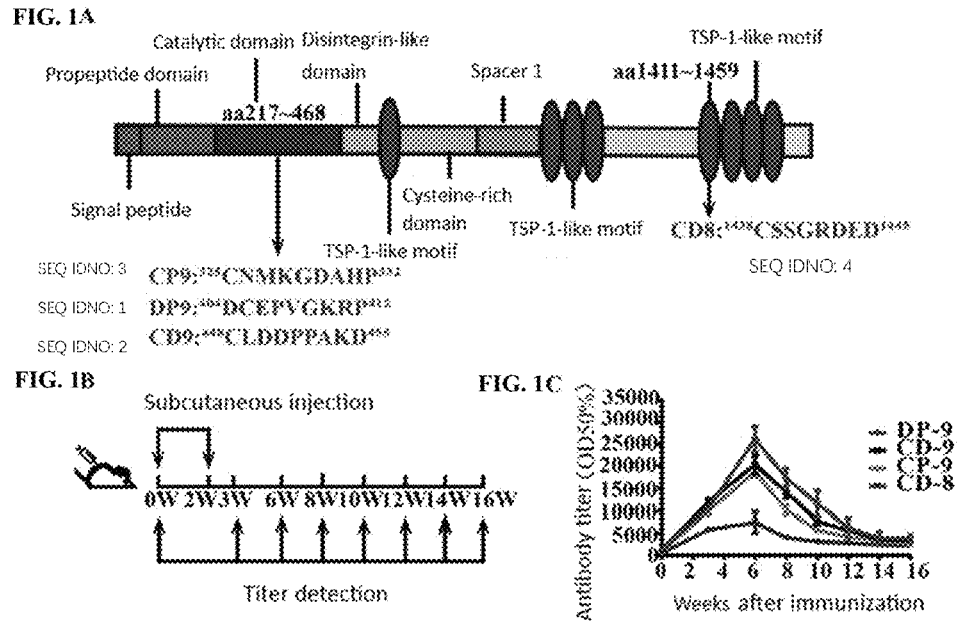
In FIGS. 1A-1C, panel 1A shows the amino acid sequences of ADAMTS-7 immunogenic peptide fragments; panel 1B is a schematic diagram of ADAMTS-7 vaccine vaccination time points and titer detection time points; panel 1C shows the titer detection results of ADAMTS-7 vaccines.
Figures 2A, 2B, 2C, 2D, 2E, 2F, 2G:
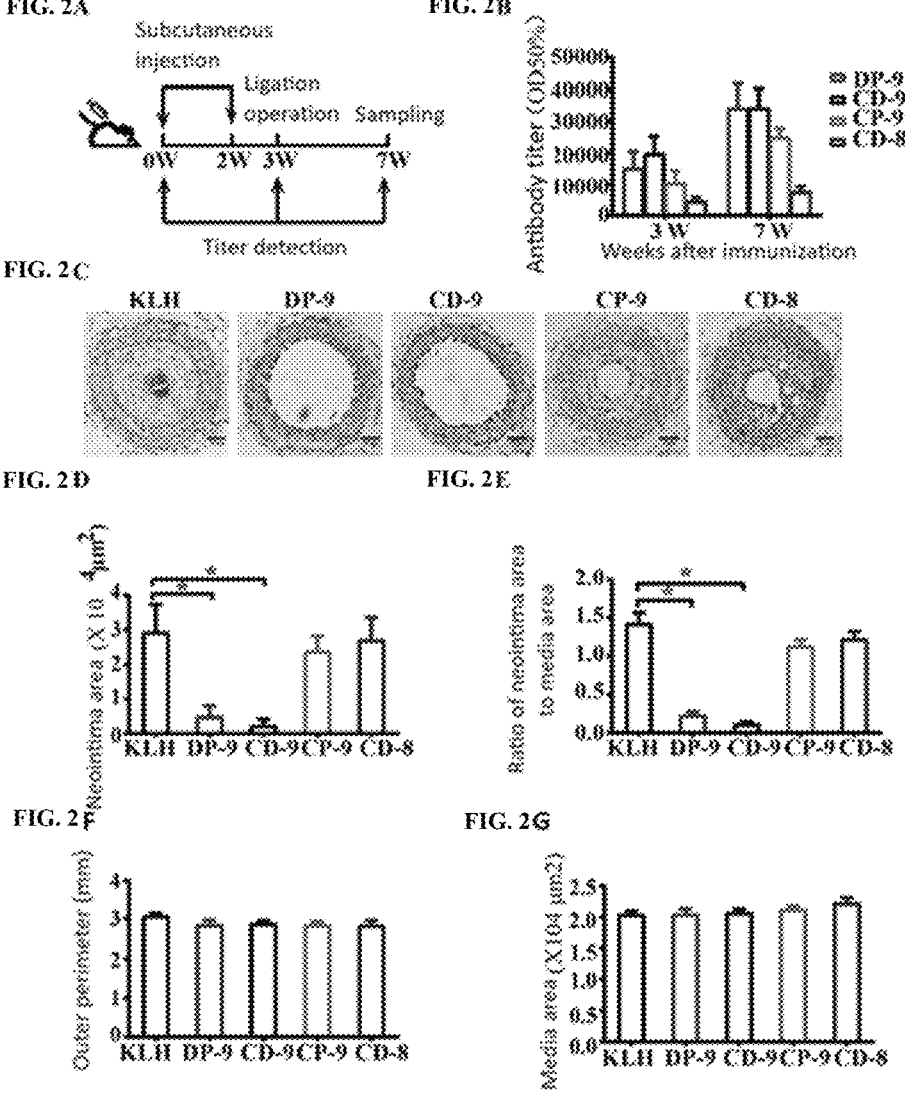
In FIGS. 2A-2G, panel 2A is a schematic diagram of ADAMTS-7 vaccine vaccination time points, titer detection time points and common carotid artery ligation operation time point; panel 2B shows the titer detection results of ADAMTS-7 vaccines; panel 2C shows the HE staining results; panel 2D shows the neointima areas of ligation model mice; panel 2E shows the ratios of neointima area to media area of ligation model mice; panel 2F shows the perimeters of the outer elastic plates (i.e., outer perimeters) of ligation model mice; panel 2G shows the media areas of ligation model mice.
Figures 3, 3B, 3E:
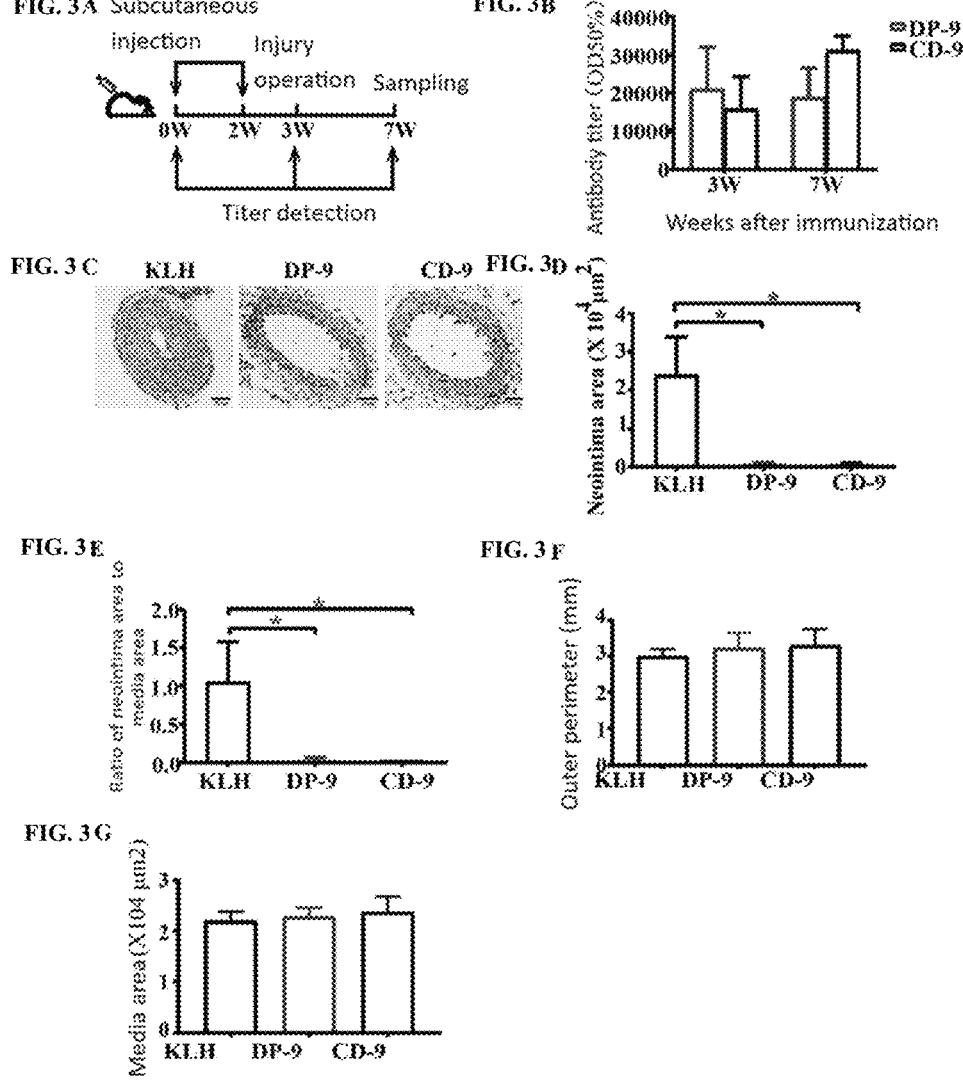
Figures 4A, 4B, 4C, 4D, 4E:
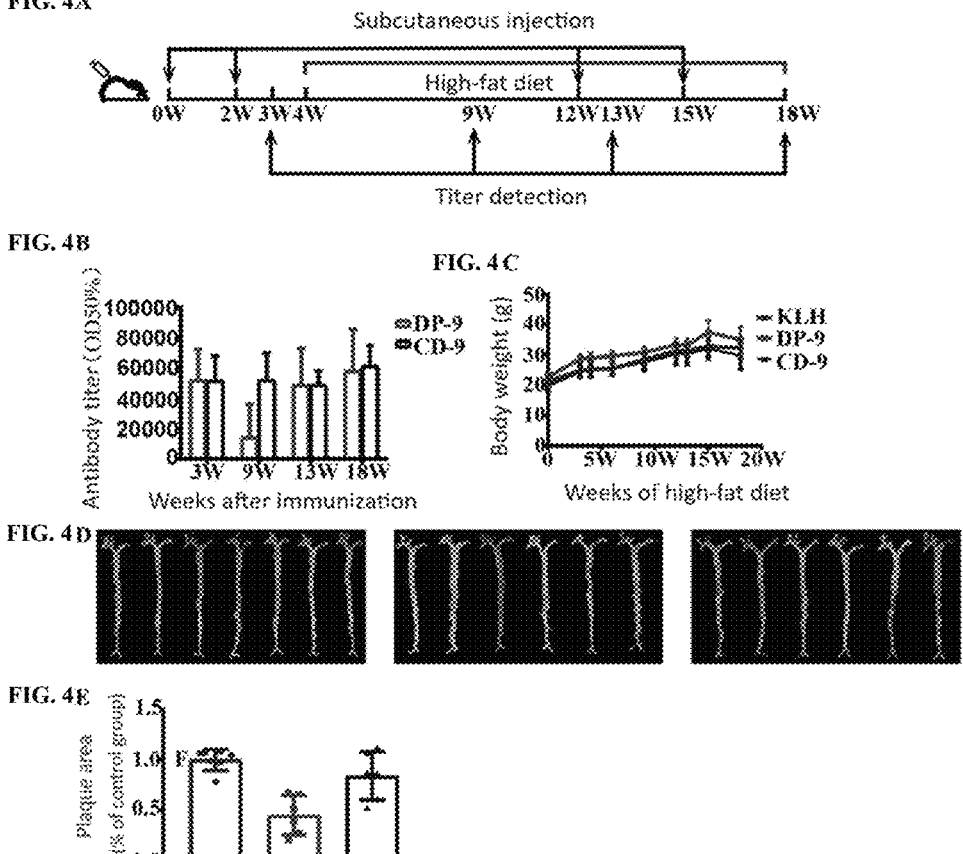
In FIGS. 4A-4E, panel 4A is a schematic diagram of ADAMTS-7 vaccine vaccination time points, titer detection time points and high-fat diet time points; panel 4B shows the titer detection results of ADAMTS-7 vaccines; panel 4C shows the detection results of mouse body weight; panel 4D shows the plaque areas of atherosclerosis model mice (control group, experimental group 1 and experimental group 2 from left to right); panel 4E shows the statistical results of plaque areas of atherosclerosis model mice.

ADAMTS7 mainly binds to and then degrades COMP, thereby promoting the migration of VSMCs and the formation of vascular neointima. The present invention selected the catalytic domain and the 4 TSP-1 like domain as the target regions for screening short peptides. By entering the amino acid sequences of the catalytic domain and the 4 TSP-1 like domain into the dialog box of IEDB B Cell Epitope Prediction respectively, predicted scores were obtained. In the higher scores, using 8, 9, 10, 11, and 12 amino acids as units, short peptides with higher overall scores were selected. Meanwhile, the amino acid sequences of the above two domains were entered into the dialog box of IEDB, the existing Crystal Structure Of Adamts4 With Inhibitor Bound which has the highest similarity with ADAMTS7 was selected as the model for epitope prediction. By combining the two results, according to the comparison results of human and mouse ADAMTS7 molecule sequences, the preliminary short peptide sequences were selected based on the standard of no difference of more than 2 amino acids. The screened short peptide sequences were then aligned with the protein molecule sequences of ADAMTS family and other protein sequences by tools such as PIR Peptide Match and BLAST, and the short peptide sequences with lower homology were selected as far as possible. Based on the above principles, four immunogenic peptide fragments (four short peptides) were screened out. The results are shown in FIGS. 1A-1C, panel 1A, and the four immunogenic peptide fragments were respectively:

```
DP9:
                                        (SEQ ID NO: 1)
    DCEPVGKRP

CD9:
                                        (SEQ ID NO: 2)
    CLDDPPAKD

CP9:
                                        (SEQ ID NO: 3)
    CNMKGDAHP

CD8:
                                        (SEQ ID NO: 4)
    CSSGRDED.
```

2. Preparation of Conjugates

The four immunogenic peptide fragments were respectively conjugated to keyhole limpet hemocyanin (KLH) using the heterobifunctional cross-linking agent Sulfo-SMCC (purchased from Thermofisher, Item No.: 22122), and the steps were as follows: (1) 2 mg of Sulfo-SMCC agent was weighed, fully dissolved in 400 μL of pure water and then added to 20 mg of KLH (10 mg/mL), mixed well and placed at room temperature for 30 minutes to obtain an activated carrier; (2) the activated carrier was added to a 100K TFF concentration column (Merck-Millipore), 50 mM PBS (containing 1 mM EDTA, pH 7.2) was added and the mixture was centrifuged 3 times at 5000 g to remove free Sulfo-SMCC, and a purified carrier was obtained; (3) about 5 mg of the short peptide (DP9, CD9, CP9 or CD8) was weighed, fully dissolved in 1 mL of 50 mM PBS (containing 1 mM EDTA, pH 7.2) and then added to the purified carrier, reacted at room temperature for 1 hour, and shaken gently every 20 minutes to obtain a vaccine mixture; (4) the vaccine mixture was added to a 100K TFF concentration column, and centrifuged three times at 5000 g to remove free and unreacted corresponding short peptide.

Four conjugate dry powders, i.e., KLH-CP9 (the conjugate obtained by coupling CP9 and KLH), KLH-DP9 (the conjugate obtained by coupling DP9 and KLH), KLH-CD9 (the conjugate obtained by coupling CD9 and KLH) and KLH-CD8 (the conjugate obtained by coupling CD8 and KLH), were finally obtained through the above coupling reaction.

3. Titer Detection

A total of 40 experimental mice, 6-week-old male C57BL/6 mice weighing 21-23 g (purchased from the Animal Department of Peking University Health Science Center) were randomly divided into 5 groups with 8 mice in each group, namely experimental group 1, experimental group 2, experimental group 3, experimental group 4 and control group.

The four conjugate dry powders obtained in step 2 were respectively dissolved in sterile normal saline to obtain four conjugate solutions with a concentration of 1 mg/mL. The four conjugate solutions were respectively mixed with aluminum hydroxide adjuvant (purchased from HEART, Item No.: BF040) in a volume ratio of 10:1 to obtain four vaccines, i.e., vaccine CP-9, vaccine DP-9, vaccine CD-9 and vaccine CD-8. The four vaccines were injected into the mice in experimental group 1, experimental group 2, experimental group 3, and experimental group 4 by subcutaneous injection at 3-4 points respectively. KLH was dissolved in sterile normal saline to obtain KLH solution with a concentration of 1 mg/mL, and the KLH solution was mixed with aluminum hydroxide adjuvant (purchased from HEART, Item No.: BF040) in a volume ratio of 10:1 to obtain a KLH mixture. The KLH mixture was injected into the mice in control group by subcutaneous injection at 3-4 points. The injected dose of each mouse in experimental groups 1 to 4 was 50 μg (based on the conjugate), and the injected dose of each mouse in control group was 50 μg (based on KLH). As shown in FIGS. 1A-1C, panel 1B, a total of two injections were performed. The first vaccine injection was performed at the age of 6 weeks (recorded as the 0th week, i.e., 0 W) and mouse tail blood was taken for the first titer detection. The second vaccine injection was performed at the 2nd week, and at the 3rd, 6th, 8th, 10th, 12th, 14th and 16th weeks, mouse tail blood was taken for titer detection. The titer detection results are shown in FIGS. 1A-1C, panel 1C. It can be seen from the figure that after immunization of mice with the four vaccines, antibody titers lasting more than 12 weeks were able to be generated.

The titer detection method of the above-mentioned vaccines was as follows: (1) 100 μl of mouse serum of experimental groups 1 to 4 of different doubling dilution ratios was added in each well of a coated ELISA plate, and the mouse serum of control group was also added; the plate was incubated at 370 for 1.5 hours; (2) the plate was washed with PBST for 5 times and patted dry, added with 100 μl of diluted HRP-labeled secondary antibody and incubated at 37° for 0.5 hours; (3) the plate was washed with PBST for 5 times and patted dry, and 100 μl of TMB (purchased from Biolegend, Item No.: 421106) was added to each well; when the control well was about to turn blue, 100 μl of diluted hydrochloric acid to was added to each well to stop the reaction, the absorption value $A_{450}$ was measured with a microplate reader, and the maximum dilution ratio was calculated when the serum reading of the mice in experimental groups 1 to 4 was greater than 2.1 times the serum reading of the mice in control group. Among them, there were 4 types of coated ELISA plates, which were an ELISA plate with the coating antigen BSA-CP9, an ELISA plate with the coating antigen BSA-DP9, an ELISA plate with the coating antigen BSA-CD9 and an ELISA plate with the coating antigen BSA-CD8. BSA-CP9, BSA-DP9, BSA-CD9 and BSA-CD8 were obtained by coupling short peptides (CP9, DP9, CD9 or CD8) with bovine serum albumin (BSA) according to the coupling method in step 2. The coating method of the ELISA plate was as follows: (1) the coating antigen was dissolved in carbonate coating buffer (pH9.6) to a concentration of 15 μg/ml, the coating antigen solution was added to a 96-well ELISA plate (purchased from Biolegend, Item No.: 423501) with a volume of 100 μl/well, and the plate was placed at 4° overnight; (2) the next day, the coating solution was discarded and patted dry, 120 μl of 1% BSA (purchased from Solarbio, Item No.: A8020-100) was added to each well to block at 370 for 1.5 hours and then the liquid was discarded and the plate was patted dry.

Example 2. Vaccine DP-9 and Vaccine CD-9 Inhibit Neointima Formation in Ligation Model 1. Establishment of Left Common Carotid Artery Ligation Model in Immunized Mice A total of 40 experimental mice, 6-week-old male C57BL/6 mice weighing 21-23 g (purchased from the Animal Department of Peking University Health Science Center) were randomly divided into 5 groups with 8 mice in each group, namely experimental group 1, experimental group 2, experimental group 3, experimental group 4 and control group.

The four conjugate dry powders (KLH-CP9, KLH-DP9, KLH-CD9 and KLH-CD8) obtained in step 2 in Example 1 were respectively dissolved in sterile normal saline to obtain four conjugate solutions with a concentration of 1 mg/mL. The four conjugate solutions were respectively mixed with aluminum hydroxide adjuvant (purchased from HEART, Item No.: BF040) in a volume ratio of 10:1 to obtain four vaccines, i.e., vaccine CP-9, vaccine DP-9, vaccine CD-9 and vaccine CD-8. The four vaccines were injected into the mice in experimental group 1, experimental group 2, experimental group 3 and experimental group 4 by subcutaneous injection at 3-4 points respectively. KLH was dissolved in sterile normal saline to obtain KLH solution with a concentration of 1 mg/mL, and the KLH solution was mixed with aluminum hydroxide adjuvant (purchased from HEART, Item No.: BF040) in a volume ratio of 10:1 to obtain a KLH mixture. The KLH mixture was injected into the mice in control group by subcutaneous injection at 3-4 points. The injected dose of each mouse in experimental groups 1 to 4 was 50 μg (based on the conjugate), and the injected dose of each mouse in control group was 50 μg (based on KLH). As shown in FIGS. 2A-2G, panel 2A, the first vaccine injection was performed at the age of 6 weeks (recorded as the 0th week, i.e. 0 W) and mouse tail blood was taken for the first titer detection and body weight measurement was performed, and the second vaccine injection was performed at the 2nd week and at the 3rd week, mouse tail blood was taken for the second titer detection, wherein the titer detection method was the same as that in Example 1. As shown in FIGS. 2A-2G, panel 2B, the mice at the 3rd week after immunization were subjected to left common carotid artery ligation experiment (i.e., modeling): before the experiment, 150 μl of 1% pentobarbital sodium was intraperitoneally injected, and the ligation was performed near the bifurcation of the common carotid artery using 6-0 suture (purchased from HARVEYBIO, Item No.: FX-6-0). Four weeks after modeling (i.e., the 7th week), mouse tail blood was taken for the third titer detection. The titer results of the vaccines are shown in FIGS. 2A-2G, panel 2B. It can be seen from the figure that the four vaccines were able to produce higher antibody titers in mice 3 weeks and 7 weeks after immunization.

2. Inhibition of Neointima

Four weeks after modeling, samples were fixed in 4% paraformaldehyde overnight and then embedded in OCT (purchased from US SAKURA, Item No.: 4583) gel, and stored at −80° C. for subsequent frozen sections. Frozen sections were prepared at six positions of 200 μm, 350 μm, 500 μm, 1 mm, 1.5 mm and 2 mm from the ligation site, each section was 7 μm, and then HE staining was performed. The staining results of each group of mice are shown in FIGS. 2A-2G, panel 2C. The four indexes of neointima area, ratio of neointima area to media area, outer elastic plate perimeter and media area were calculated. The results are shown in panels 2D, 2E, 2F and 2G in FIGS. 2A-2G, and Image Pro Plus software was used for statistics analysis: the vascular neointima area and the ratio of intima area to media area in mice with ligated common carotid artery after injection of vaccine DP-9 (indicated by "DP-9" in the figure) or CD-9 (indicated by "CD-9" in the figure) were significantly lower than that of control group (indicated by "KLH" in the figure); meanwhile, there were no statistical differences in the vascular neointima area and the ratio of intima area to media area in mice injected with vaccine CP-9 (indicated by "CP-9" in the figure) or CD-8 (indicated by "CD-8" in the figure) and that of control group (indicated by "KLH" in the figure). Therefore, vaccine DP-9 and vaccine CD-9 have significant effects on inhibiting neointima formation caused in the ligation model.

Example 3. Vaccine DP-9 and Vaccine CD-9 Inhibit Neointima Formation in Guide Wire Injury Model 1. Establishment of Guide Wire Injury Model in Immunized Mice A total of 30 experimental mice, 6-week-old male C57BL/6 mice weighing 21-23 g (purchased from the Animal Department of Peking University Health Science Center) were randomly divided into 5 groups with 6 mice in each group, namely experimental group 1, experimental group 2, experimental group 3, experimental group 4 and control group.

The four conjugate dry powders (KLH-CP9, KLH-DP9, KLH-CD9 and KLH-CD8) obtained in step 2 in Example 1 were respectively dissolved in sterile normal saline to obtain four conjugate solutions with a concentration of 1 mg/mL. The four conjugate solutions were respectively mixed with aluminum hydroxide adjuvant (purchased from HEART, Item No.: BF040) in a volume ratio of 10:1 to obtain four vaccines, i.e., vaccine CP-9, vaccine DP-9, vaccine CD-9 and vaccine CD-8. The four vaccines were injected into the mice in experimental group 1, experimental group 2, experimental group 3 and experimental group 4 by subcutaneous injection at 3-4 points respectively. KLH was dissolved in sterile normal saline to obtain KLH solution with a concentration of 1 mg/mL, and the KLH solution was mixed with aluminum hydroxide adjuvant (purchased from HEART, Item No.: BF040) in a volume ratio of 10:1 to obtain a KLH mixture. The KLH mixture was injected into the mice in control group by subcutaneous injection at 3-4 points. The injected dose of each mouse in experimental groups 1 to 4 was 50 μg (based on the conjugate), and the injected dose of each mouse in control group was 50 μg (based on KLH). As shown in FIGS. 3A-3G, panel 3A, the first vaccine injection was performed at the age of 6 weeks (recorded as the 0th week, i.e. 0 W) and mouse tail blood was taken for the first titer detection and body weight measurement was performed, and the second vaccine injection was performed at the 2nd week and at the 3rd week, mouse tail blood was taken for the second titer detection, wherein the titer detection method was the same as that in Example 1. As shown in FIGS. 3A-3G, panel 3B, the mice after immunization were subjected to left common carotid artery guide wire injury experiment (i.e., modeling): before the experiment, 150 μl of 1% pentobarbital sodium was intraperitoneally injected; after the neck skin was sterilized, an anterior median incision was made in the neck, the external carotid artery was ligated, and the blood flow of the internal carotid artery and common carotid artery was temporarily blocked with a vascular clamp; micro vannas scissors were used to cut an oblique opening near the ligation site of the distal end of the external carotid artery, a metal guide wire with a diameter of 0.38 mm was inserted, and it was rotated forward and backward 5 times to rub the vessel wall, causing damage to the common carotid artery; the guide wire was withdrawn, the proximal end of the incision of the artery was ligated, and the skin was sutured. Four weeks after modeling (i.e., the 7th week), mouse tail blood was taken for the third titer detection. The titer results of the vaccines are shown in FIG. 3A-3G, panel 3B. It can be seen from the figure that vaccines CP-9 and DP-9 were able to produce higher antibody titers in immunized mice.

2. Inhibition of Neointima

Four weeks after modeling, samples were fixed in 4% paraformaldehyde overnight and then embedded in OCT (purchased from US SAKURA, Item No.: 4583) gel, and stored at −80° C. for subsequent frozen sections. Frozen sections were prepared at six positions of 200 μm, 350 μm, 500 μm, 1 mm, 1.5 mm and 2 mm from the ligation site, each section was 7 μm, and then HE staining was performed. The staining results of each group of mice are shown in FIGS. 3A-3G, panel 3C. The four indexes of neointima area, ratio of intima area to media area, outer elastic plate perimeter and media area were calculated. The results are shown in panels 3D, 3E, 3F and 3G in FIGS. 3A-3G, and Image Pro Plus software was used for statistics analysis: the neointima area and the ratio of intima area to media area in mice with common carotid artery injured by guide wire after injection of vaccine DP-9 (indicated by "DP-9" in the figure) or CD-9 (indicated by "CD-9" in the figure) were significantly lower than that of control group (indicated by "KLH" in the figure). Therefore, vaccine DP-9 and vaccine CD-9 have significant effects on inhibiting neointima formation caused in the guide wire injury model.

Example 4. Vaccine DP-9 Inhibits Atherosclerosis Formation Induced by High-Fat Feeding in LDLR−/− Mice 1. Establishment of Atherosclerosis Model A total of 18 experimental mice, 8-week-old male LDLR−/− mice weighing 23-25 g (purchased from the Animal Department of Peking University Health Science Center) were randomly divided into 3 groups with 6 mice in each group, namely experimental group 1, experimental group 2 and control group.

The two conjugate dry powders (KLH-DP9 and KLH-CD9) obtained in step 2 in Example 1 were respectively dissolved in sterile normal saline to obtain two conjugate solutions with a concentration of 1 mg/mL. The two conjugate solutions were respectively mixed with aluminum hydroxide adjuvant (purchased from HEART, Item No.: BF040) in a volume ratio of 10:1 to obtain two vaccines, i.e., vaccine DP-9 and vaccine CD-9. They were injected into the mice in experimental group 1 and experimental group 2 by subcutaneous injection at 3-4 points respectively. KLH was dissolved in sterile normal saline to obtain KLH solution with a concentration of 1 mg/mL, and the KLH solution was mixed with aluminum hydroxide adjuvant (purchased from HEART, Item No.: BF040) in a volume ratio of 10:1 to obtain a KLH mixture. The KLH mixture was injected into the mice in control group by subcutaneous injection at 3-4 points. The injected dose of each mouse in experimental groups 1 and 2 was 50 μg (based on the conjugate), and the injected dose of each mouse in control group was 50 μg (based on KLH). As shown in FIGS. 4A-4E, panel 4A, the first vaccine injection was performed at the age of 8 weeks (recorded as the 0th week, i.e. 0 W) and the vaccine injections were performed at the 2nd, 4th, 12th, and 15th weeks respectively; from the 4th week to the 18th week, the mice were given an atherogenic diet (i.e., a high-fat diet feed, purchased from Research Diets, Item No.: D12108C, the main components of which were 1.25% cholesterol, 40 kcal % fat); at the 3rd, 9th, 13th and 18th weeks, the titer detection of vaccines and body weight measurement were carried out, wherein the titer detection method was the same as that in Example 1. As shown in FIGS. 4A-4E, panels 4B and 4C, the results show that vaccines CD-9 and DP-9 were able to produce higher antibody titers in immunized mice, and the higher antibody titers were still detectable at the 18th week.

2. Inhibition of Atherosclerosis Formation

Under a microscope, the entire blood vessel of the mouse was dissected out with microscopic instruments, and then fixed in 4% paraformaldehyde for 6 hours, soaked in 60% isopropanol for 5 minutes, stained with oil red O for 30 minutes in the dark; then the floating color was washed in 60% isopropanol, and then the adventitial fat was peeled off under the microscope; after peeling off, the blood vessel was longitudinally dissected with micro scissors, and the same steps of soaking in 60% isopropanol for 5 minutes, then staining with Oil Red O for 30 minutes in the dark, and then washing off the floating color in 60% isopropanol were repeated; finally, the stained blood vessel was fixed on a plate to obtain general pictures, as shown in FIGS. 4A-4E, panel 4D. Atherosclerotic plaques were formed in control group, experimental group 1 and experimental group 2. Image Pro Plus software was used to calculate the plaque areas, and taking the plaque area of control group (indicated by "KLH" in the figure) as 1, the relative plaque areas of experimental group 2 (indicated by "CD-9" in the figure) and experimental group 1 (indicated by "DP-9" in the figure) were calculated. The results show that: compared with the control group (represented by "KLH" in the figure), the relative plaque area of experimental group 1 (indicated by "DP-9" in the figure) was significantly reduced (p<0.001), and the relative plaque area of experimental group 2 (indicated by "CD-9" in the figure) had no difference (p>0.05), indicating that vaccine DP-9 significantly inhibited the formation of atherosclerotic plaques, and there was no significant difference between vaccine CD-9 and control group KLH.

The present invention adopted the following statistical methods for analysis: (1) the continuous random variables of normal distribution were represented by mean±standard error (Mean±SEM); (2) paired t test (two-sided test) was used for all paired data; (3) group t test (two-sided test) was used for unpaired data; (4) One-way ANOVA was used for the comparison of one-way results between multiple groups, and Student-Newman-Keuls test was used for further comparing between two groups; (5) Two-way ANOVA was used for the comparison of two-way results between multiple groups, and Bonferroni test was used for further comparing between two groups.

The present invention has been described in detail above. For those skilled in the art, without departing from the spirit and scope of the present invention, and without unnecessary experimentation, the present invention can be implemented in a wide range under equivalent parameters, concentrations and conditions. While the present invention has given particular examples, it should be understood that the present invention can be further modified. In conclusion, in accordance with the principles of the present invention, the present application is intended to cover any alterations, uses or improvements of the present invention, including changes made using conventional techniques known in the art, departing from the scope disclosed in this application. The application of some of the essential features can be made within the scope of the following appended claims.

INDUSTRIAL APPLICATION

1. The short peptides of metalloprotease ADAMTS-7 screened by the present invention can cause specific immune responses in wild-type C57BL/6 mice and ApoE-/- mice, and produce specific antibodies against the short peptides, which can specifically bind to the catalytic region of metalloprotease ADAMTS-7 and block its hydrolase activity.

2. The vaccines prepared by the present invention can significantly inhibit the intimal neogenesis in the vascular restenosis mouse models (i.e., the ligation model and the guide wire injury model), and the occurrence of atherosclerosis in high-fat-fed mice, and can be used for the prevention or treatment of atherosclerosis and/or vascular restenosis.

3. The heterobifunctional cross-linking agent used in the preparation of the vaccines of the present invention has the characteristics of being able to linking two groups at the same time, and different groups can be linked successively in two steps, and the operation is simple and fast.

The invention claimed is:

1. A product, which is one of the following (A) or (B):

(A) a peptide consisting of the amino acid sequence shown in SEQ ID NO: 1 of the sequence listing, wherein the peptide does not exist as an isolated fragment in nature;

and the peptide is obtained by:

(i) epitope prediction using IEDB B Cell Epitope Prediction;

(ii) structural modeling based on the crystal structure of ADAMTS-4; and (iii) homology alignment with ≤2 amino acid differences from mouse ADAMTS-7; or (B) a conjugate of a peptide, wherein the conjugate consists of a peptide, a carrier protein and a heterobifunctional cross-linking agent, and the conjugate is a complete antigen obtained by coupling the peptide with a carrier protein via a heterobifunctional cross-linking agent; and wherein the peptide is a peptide consisting of the amino acid sequence shown in SEQ ID NO: 1 of the sequence listing;

the carrier protein is selected from keyhole limpet hemocyanin, recombinant Qβ phage particle protein, recombinant bovine papilloma virus protein, recombinant hepatitis B virus protein or tetanus toxoid; and the heterobifunctional cross-linker is selected from SMCC, Sulfo-SMCC, or LC-SMCC.

2. A vaccine for preventing or treating atherosclerosis and/or preventing or treating vascular restenosis and/or reducing the neointima area of damaged arteries and/or reducing the ratio of intima area to media area of damaged arteries, consisting of the product according to claim 1 and an immune adjuvant;

wherein the immune adjuvant is selected from aluminum hydroxide adjuvant, alum adjuvant or Freund's adjuvant.

3. A method for preventing or treating atherosclerosis and/or preventing or treating vascular restenosis and/or reducing the neointima area of damaged arteries and/or reducing the ratio of intima area to media area of damaged arteries, comprising:

the step of administering a product of claim 1 or a vaccine comprising the product of claim 1 to an animal to prevent or treat atherosclerosis and/or prevent or treat vascular restenosis and/or reduce the neointima area of damaged arteries and/or reduce the ratio of intima area to media area of damaged arteries wherein the product is one of the following (A) or (B):

(A) a peptide consisting of the amino acid sequence shown in SEQ ID NO: 1 of the sequence listing, wherein the peptide does not exist as an isolated fragment in nature;

and the peptide is obtained by:

(i) epitope prediction using IEDB B Cell Epitope Prediction;

(ii) structural modeling based on the crystal structure of ADAMTS-4; and (iii) homology alignment with ≤2 amino acid differences from mouse ADAMTS-7; or (B) a conjugate of a peptide, wherein the conjugate consists of a peptide, a carrier protein and a heterobifunctional cross-linking agent, and the conjugate is a complete antigen obtained by coupling the peptide with a carrier protein via a heterobifunctional cross-linking agent; and wherein the peptide consists of the amino acid sequence shown in SEQ ID NO: 1 of the sequence listing;

the carrier protein is selected from keyhole limpet hemocyanin, recombinant Qβ phage particle protein, recombinant bovine papilloma virus protein, recombinant hepatitis B virus protein or tetanus toxoid; and the heterobifunctional cross-linker is selected from SMCC, Sulfo-SMCC, or LC-SMCC.

\*   \*   \*   \*   \*